United States Patent [19]

Lipman

[11] Patent Number: 5,941,833
[45] Date of Patent: Aug. 24, 1999

[54] HEATBEAM DOLORIMETER FOR PAIN AND SENSORY EVALUATION

[75] Inventor: Jonathan J. Lipman, Libertyville, Ill.

[73] Assignee: Neuroscience Toolworks, Inc., Libertyville, Ill.

[21] Appl. No.: 08/868,632

[22] Filed: Jun. 4, 1997

[51] Int. Cl.⁶ ........................................................ A61B 5/00
[52] U.S. Cl. ........................................... 600/555; 600/549
[58] Field of Search ........................................ 600/555, 549

[56] References Cited

U.S. PATENT DOCUMENTS

| | | | |
|---|---|---|---|
| 2,728,337 | 12/1955 | Guilleman, Jr. | 600/555 |
| 4,641,661 | 2/1987 | Kalarickal | 128/744 |
| 4,884,091 | 11/1989 | Bellak | 128/744 |
| 5,191,896 | 3/1993 | Gafni et al. | 128/742 |
| 5,230,345 | 7/1993 | Curran et al. | 128/739 |
| 5,293,876 | 3/1994 | Koltringer | 600/555 |
| 5,474,084 | 12/1995 | Cunniff | 128/744 |

OTHER PUBLICATIONS

Lipman et al., "Chronic pain assessment using heat beam dolorimetry", Pain 30:59–67 (1987).
Lipman et al., "Normal and radiculopathic cutaneous pain tolerance levels evaluated by heat–beam dolorimetry", J. Neurosurgery 72:883–888 (1990).
Rollman, "Signal detection theory pain measures: Empirical validation studies and adaptation–level effects", Pain 6:9–21 (1979).
Sriwatanakul et al., "Analysis of narcotic analgesic usage in the treatment of postoperative pain", J. Am. Med. Ass'n. 250:926–929 (1983).
Sriwatanakul et al., "Anlysis of narcotic analgesic usage in the treatment of postoperative pain", J. Am. Med. Ass'n. 250:926–929 (1983).
Lipman, "Pain Measurement", Chapter 9 in :Contemporary issues in pain measurement. Parris, WCV (ed.) Kluwer Pubs., pp. 123–146, 1991.
Chapman, "On the relationship of human laboratory and clinical pain research", in Pain Measurement and Assessment, R. Melzack (ed.), Raven Press (NY), pp. 243–249 (1983).
Lipman and Blumenkopf, "Comparison of subjective and objective analgesic effects of intravenous and intrathecal morphine on chronic pain patients by heat beam dolorimetry", Pain 39:249–256 (1989).
Svensson et al., "Quantitative determinations of sensory and pain thresholds on human oral mucosa by argon laser stimulation", Pain 49:233–239 (1992).

Primary Examiner—Max Hindenburg
Assistant Examiner—Pamela L. Wingood
Attorney, Agent, or Firm—McDonnell, Boehnen Hulbert & Berghoff

[57] ABSTRACT

The present invention provides both devices and methods for determining a subject's cutaneous pain tolerance level at any site on the body so as to provide both for examiner and subject input as well as automatic data acquisition.

The present invention fulfills a need for a devices and methods that provide a quantitative, objective measure of the pain tolerance level. The portability and automatic data acquisition capability of the present invention allow for its use as a cost-effective diagnostic tool in the general practitioner's office, thereby allowing for earlier assessment of neurological abnormalities than is possible with currently available pain measurement devices. The present invention further allows for chronic pain diagnosis, the diagnosis of subtle sensory abnormalities, and pain measurement quality assurance. The present invention is currently alone in its ability to address both the clinical and commercial needs in quantitative pain measurement.

17 Claims, 5 Drawing Sheets

HEATBEAM DOLORIMETER FOR PAIN AND SENSORY EVALUATION

The invention described herein was funded, in part, by grant number R43NS34616 from the National Institutes of Health, and is subject to a nonexclusive licensing agreement with the United States government.

1. Technical Field

The present invention relates to neurological diagnostic tools. More particularly, the present invention relates to an improved radiant heatbeam dolorimeter for determining a subject's cutaneous pain tolerance level at any site on the body.

2. Background Art

Pain is the single most common symptom for which patients seek medical treatment and there is currently no objective method available for its measurement. Present methods of quantifying "pain" are little more than lexicons for its verbal description or biomechanical methods for measuring the restriction of articular range of motion or activities of daily living associated with the pain. Some psychometric methods attempt to quantify the personality or cognitive distortions from which the pain patient suffers. In no case, however, do these methods reveal the covert and subjective sensory perception that is the pain experience in a way that can be quantified by an outside observer (for review, see Lipman 1991). The need for pain measurement methods was recently addressed by both the Social Security Administration and the United States Congress. A report ordered by Congress through the Secretary of Health and Human Services by a Commission on the Evaluation of Pain, recommended that some sort of objective measurement of pain be developed to assist in determining disability (see: Fordice 1995, Fields 1995, APS 1990).

The need for objective pain measurement goes beyond the economics of forensic disability assessment. Objective methods of pain measurement are required for accurate assessment of patient complaint and to assure appropriate treatment. For example, the need to appropriately medicate severe acute and chronic pain and also cancer pain requires an objective method of pain measurement. A corollary need is to avoid inappropriate treatment of pain—or claimed pain—where the possibility of malingering for secondary gain is a possibility. Such "secondary gains" are believed to account for an appreciable portion of chronic pain treatment demand, and forensically include the desire for disability payments, for insurance damage settlements or for other fiduciary incentives. Such secondary gains are not always conscious and may derive from psychological reasons related to the psychosocial set and setting of the patient and their disease. The inappropriate desire for opiate drugs probably accounts for a significant fraction of pain therapy prescription drug demand, yet absent any objective method of establishing the existence of "pain", the physician has no objective standards by which to prohibit such demand, and frequently feels ethically bound to take claims of pain at face value, or risk accusation of ineffective care and inhumane treatment.

Furthermore, an objective pain measurement device that is operable in the general practitioner's office would fulfill a pressing diagnostic need. It is from the general practitioner's office that referrals to neurologists are made. For example, patient complaints of subjective numbness are often not detectable on clinical examination because present diagnostic methods are not sensitive enough to detect the early stage sensory impairments of such neurological disorders as nerve root entrapment or peripheral neuropathy. As a result, patients with these types of neurological disorders cannot be diagnosed until the disorder progresses to a detectable level. The availability of a pain measurement device sensitive enough to detect the presence or absence of these and other abnormalities at an early stage would provide more effective medical intervention, or avoid unnecessary medical intervention. In order for such a device to be cost-effective for the general practitioner it should not require valuable dedicated space, and thus should be portable. Similarly, greater cost-effectiveness would be realized if the device were operable by a single person.

Basic psychophysical methods for the estimation of pain sensibility have a long history of questionable clinical relevance. Psychophysical methods seek to quantify pain intensity in an objective fashion despite the fact that pain is a complex and multi-faceted sensory mode, intrinsically containing dimensions of set, setting, ideation, memory, anxiety, and experiential import.

Subjective pain perception does not bear a simple relationship to stimulus intensity, but it nevertheless has some quantifiable dimensions and limits; a lower level of identity (the pain threshold) and an upper level of identity (the tolerance level). Below the pain threshold, stimuli of increasing intensity destined to broach this level are perceived as noxious yet non-painful (prepain). The pain threshold itself is highly labile and subject to psychological manipulation either of imposed suggestion (experimenter bias) or autosuggestion bias (the placebo response) or both. No studies have been able to demonstrate a relationship between pain threshold and the underlying pain state; in fact, pain threshold measurement procedures are unable to quantitatively demonstrate analgesic states engendered by clinically proven drugs as, for example, morphine (for review, see Chapman, et al.). Furthermore, the method suffers from major disadvantages when transferred to the clinical situation where the test subject, who may suffer excruciating pain of endogenous pathological origin, is less able to attend to the minor sensory nuances of the pain threshold.

The pain sensitivity range constitutes a psychophysical region between the pain threshold level, where prepain becomes subjectively painful, and the pain tolerance level, which represents the greatest intensity of a noxious stimulus that a subject can tolerate (Hardy et al). In contrast to the pain threshold level, the pain tolerance level is subjectively distinct and unequivocal. Further, the pain tolerance level exhibits a linear change with stimulus intensity and yet it shares a sufficient commonality with the physiological processes of endogenous pathological pain perception that are positively influenced by changes in the endogenous pain state.

Pain tolerance levels are usually assessed by the use of a continuous, rather than a discrete, noxious stimulus, the cut-off of which is always the maximum limit of the subject's subjective pain tolerance. Pain tolerance has been measured by several means including the cold pressor test in which the hand or a limb is immersed in ice water until unendurable pain results, focal pressure, tourniquet ischemia and radiant heat. (For review see Lipman, 1991.) Tolerance methods using these techniques, unlike threshold methods, also evoke some not inconsiderable anxiety and apprehension on the part of the subject, which may resemble the anxiety of the pain-suffering patient. However, studies have shown that tactile stimulation interferes with that aspect of cutaneous tolerance limit responsive to internal pain interference and thus methods that utilize a contact stimulus invalidate pain tolerance level results. While the cold pressor, focal pressure and tourniquet ischemia tests all involve tactile stimulation, radiant heat methods do not require direct contact with the subject.

The concept of a radiant heat pain stimulator for human use was initially developed by Hardy, Wolff and Goodell in 1952. However, most radiant heat pain stimulators have been designed to measure the pain threshold level and thus are prone to the disadvantages inherent in measuring pain threshold. Recently, a concept prototype heat pain stimulator was developed that measures the pain tolerance level (see Lipman, et al 1987; Lipman and Blumenkopf 1989; and Lipman, et al. 1990). The concept prototype was a nonportable, electromechanical device that did not allow for automatic data acquisition. As such, the concept prototype required dedicated laboratory space and also required one person to operate the device and a second person to record data. Accordingly, there remains a need in the art for a non-contact, radiant heatbeam dolorimeter that provides a quantitative, objective measure of the pain tolerance level, is portable and allows for automatic data acquisition.

SUMMARY OF THE INVENTION.

The present invention fulfills the need for a non-contact, radiant heatbeam dolorimeter that provides a quantitative, objective measure of the pain tolerance level, is portable and allows for automatic data acquisition. These features of the present invention allow for its use as a cost-effective diagnostic tool in the general practitioner s office, thereby allowing for earlier assessment of neurological abnormalities than is possible with currently available pain measurement devices. The present invention allows for chronic pain diagnosis, the diagnosis of subtle sensory abnormalities, and pain measurement quality assurance. The present invention is currently alone in its ability to address both the clinical and commercial needs in quantitative pain measurement.

A first object of the present invention is to provide a portable apparatus for determining a subject's cutaneous pain tolerance level at any site on the body.

According to this object, the present invention provides, as an embodiment of the invention, an improved dolorimeter which comprises a non-contact heat projector, set inside a housing assembly, for delivering a radiant heat stimulus, to cause pain in the subject; a targeting device, attached to the heat source housing assembly, for accurately positioning the heat projector for stimulus delivery; a thermopile, also attached to the heat source housing assembly, for detecting movement in response to the stimulus that indicates the subject has reached the pain tolerance level; and computer connections to the non-contact heat projector, the targeting device and the thermopile that allow the computer to control the output of the heat projector and the targeting device, and also allows automatic data acquisition from the thermopile as to movement by the subject, thereby allowing the invention to be operated by a single person.

In a preferred embodiment of the present invention, both the heat source and the targeting device are focused on the same point on a subject's skin to allow measurement of the temperature over time at the site of heat contact. When a subject moves in response to reaching the pain tolerance level, the heat source and targeting device will then be focused on a different point of the subject's skin, resulting in the targeting device recording a drop in temperature.

Additionally, in accordance with an embodiment of the present invention, the computer allows for interfacing between the computer and the subject, as well as between the computer and the computer operator, to allow for input by the subject or the operator. Moreover, in accordance with an embodiment of the present invention, the computer automatically acquires and records input from the interface between the subject and the computer, the interface between the computer and the computer operator, thereby facilitating the invention's operability by a single person.

The present invention further provides for a method of determining a subject's cutaneous pain tolerance level at any site on the body.

According to this object, the present invention discloses, as an embodiment of the invention a method which comprises providing a portable apparatus comprising:

a non-contact heat projector, set inside a housing assembly, for delivering a radiant heat stimulus, to cause pain in the subject; a targeting device, attached to the heat source housing assembly, for accurately positioning the heat projector for stimulus delivery; a thermopile, also attached to the heat source housing assembly, for detecting movement in response to the stimulus that indicates the subject has reached the pain tolerance level; and computer connections to the non-contact heat projector, the targeting device and the thermopile that allow the computer to control the output of the heat projector and the targeting device, and also allows automatic data acquisition from the thermopile as to movement by the subject, thereby allowing the invention to be operated by a single person. Additionally, in accordance with an embodiment of the present invention, the computer allows for interfacing between the computer and the subject, as well as between the computer and the computer operator, to allow for input by the subject or the operator. Moreover, in accordance with an embodiment of the present invention, the computer automatically acquires and records input from the interface between the subject and the computer, the interface between the computer and the computer operator, thereby facilitating the invention's operability by a single person.

The method of the invention further comprises initiating a stimulus of a controlled intensity from the non-contact heat projector; monitoring the time interval between initiation of the stimulus and detection by the thermopile that the subject has reached pain tolerance level, the interval, or the power-time integral thereof, being a measure of pain tolerance latency at the monitoring site, and automatically acquiring and recording the pain tolerance latency data generated by the thermopile via the computer connection with the thermopile.

Moreover, in accordance with an embodiment of the present invention, the computer processes the pain tolerance latency data to obtain statistical data, which it stores.

Finally, in accordance with an embodiment of the present invention, the computer displays both the pain tolerance latency data and statistical data obtained by processing the pain tolerance latency data.

DETAILED DESCRIPTION OF PREFERRED EMBODIMENTS

Figure 1A:
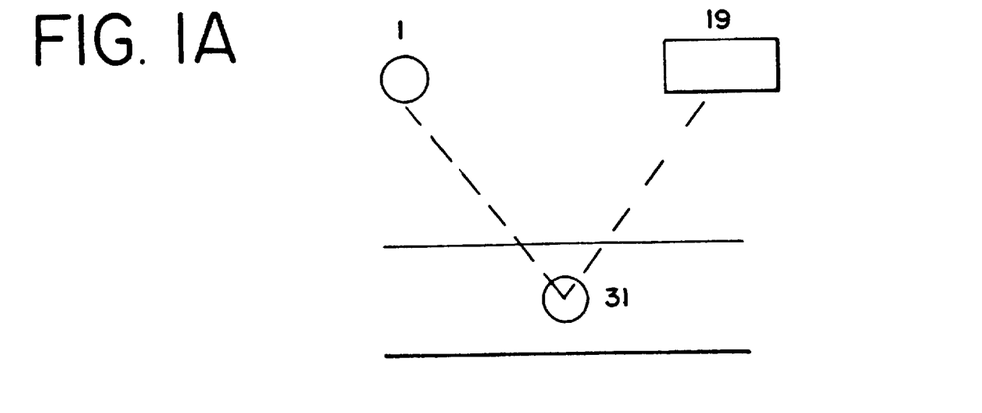
FIG. 1A and 1B are illustrations of the operation of the dolorimeter.
Figure 1B:
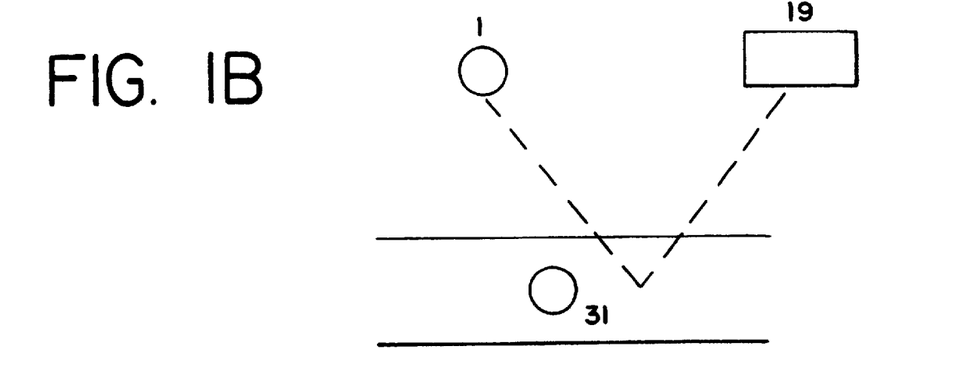
Figure 2:
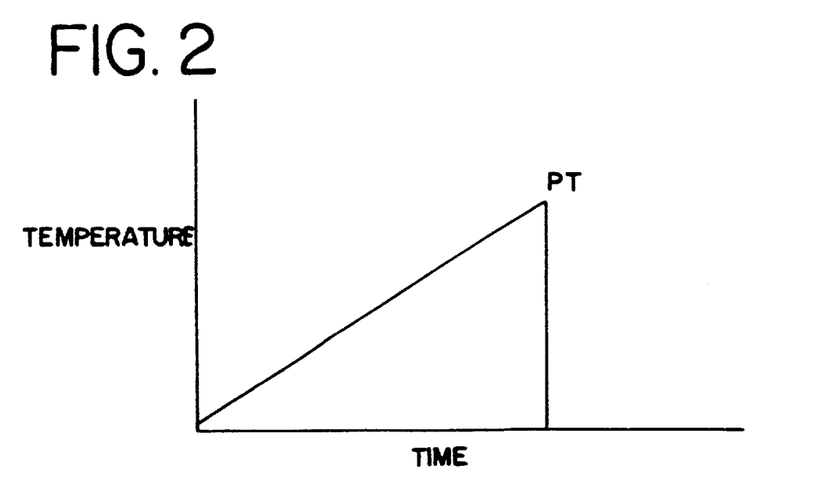
FIG. 2 is a representative graph recording the change in temperature over time measured by the targeting device of the dolorimeter.

Referring to FIG. 1A–1B there is illustrated a method for determining a subject's cutaneous pain tolerance level at any site on the body. As illustrated in FIG. 1A a heat source 1 and a targeting device 19 are focused on the same site of a subject's skin 31 where the pain tolerance level is to be measured. The targeting device 19 continually measures the increase in skin temperature caused by the heat source 1 at that site on the subject's skin 31. Upon reaching the pain tolerance level (PT), the subject moves and thereby the site that the heat source 1 and targeting device 19 are focused upon changes (FIG. 1A) to a previously unheated site. As a result or reaching the pain tolerance level (PT), the targeting device records a sharp drop in temperature at the site of focus, as illustrated in FIG. 2. In a preferred embodiment, the targeting device comprises an infrared-sensing thermopile, such as an Omega OP65 device.

Figure 3:
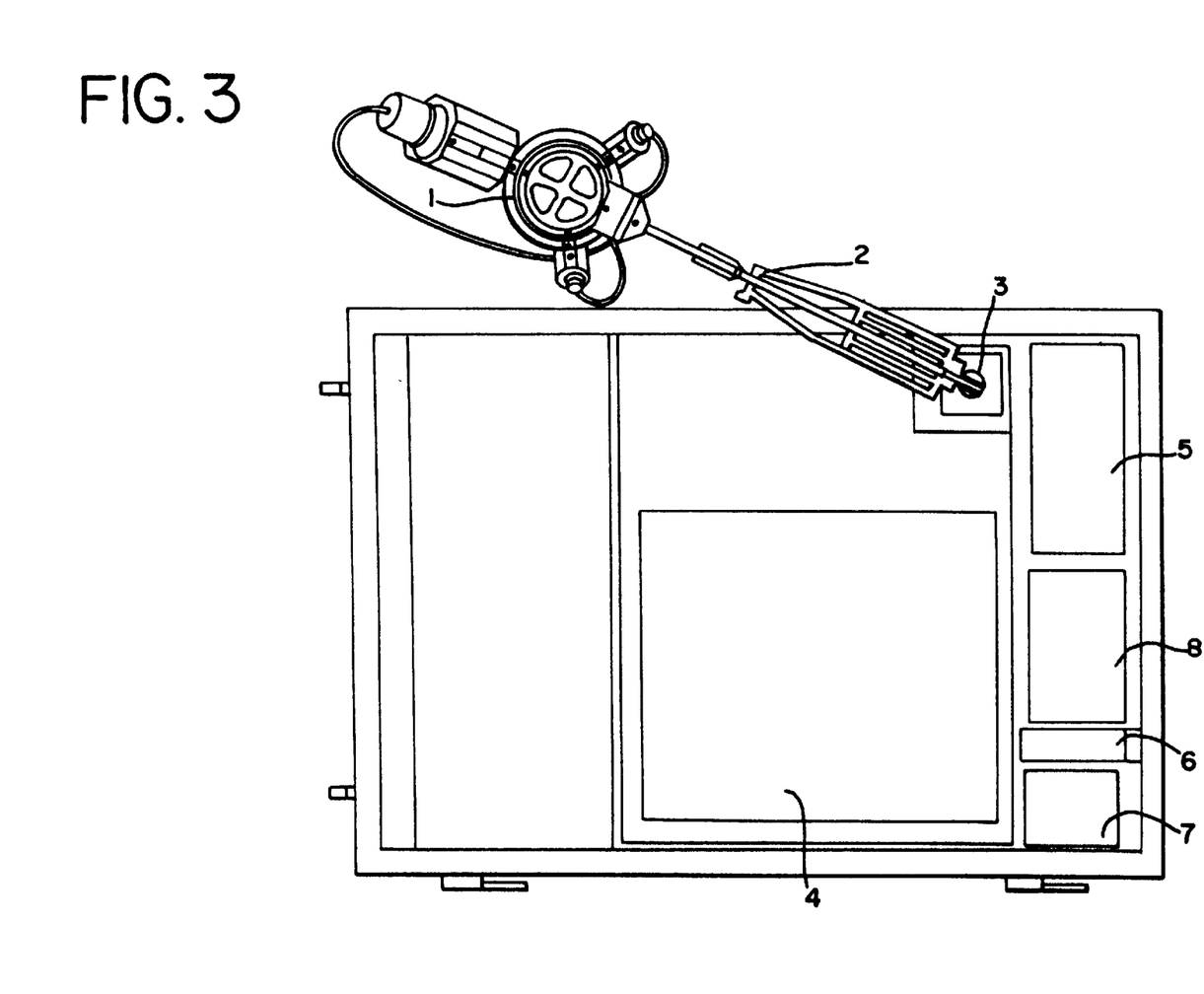
FIG. 3 is a generalized block diagram illustration of a top view of the dolorimeter instrument package in accordance with a preferred embodiment of the invention.

Referring now to FIG. 3, there is illustrated a portable apparatus for determining a subject's cutaneous pain tolerance level at any site on the body in accordance with a preferred embodiment of the invention. The apparatus comprises a heating head I associated with a double linkage parallelogram arm 2, preferably fabricated out of hollow steel tubing. The linkage arm is further connected to a pivot base 3, which is present in the dolorimeter instrument package. The dolorimeter instrument package is encased in a portable container and comprises, in addition to the pivot base, a lap top computer 4, such as an IBM 760C portable computer, which receives electrical power from an internal battery. The computer has two PCMCIA card slots, and one of the slots contains an interface card, such as a ComputerBoards PCM-DAS 16/12D interface card. This card contains four digital inputs, 8 differential analog-to-digital input channels and four digital outputs. The internal computer battery inputs its voltage status to the computer via a differential analog-to-digital input channel. Associated with the computer in the dolorimeter instrument package is a battery 5 to provide electrical power to the components of the heatbeam dolorimeter, an electrical strip 6, a battery charger 7 for recharging the heatbeam dolorimeter battery and the computer battery, and a lap top computer power supply 8.

Figure 4:
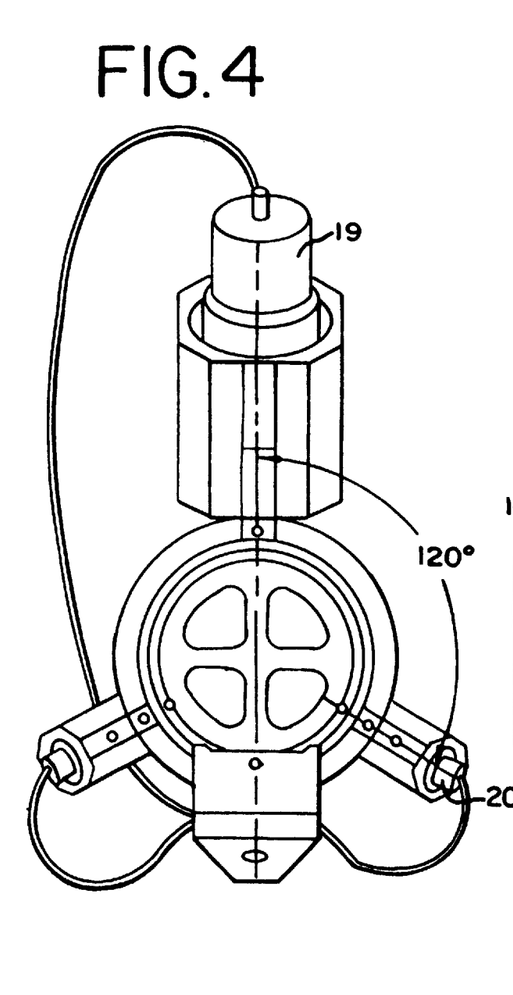
FIG. 4 is a side view of an assembled dolorimeter heating assembly in accordance with a preferred embodiment of the invention.
Figure 5:
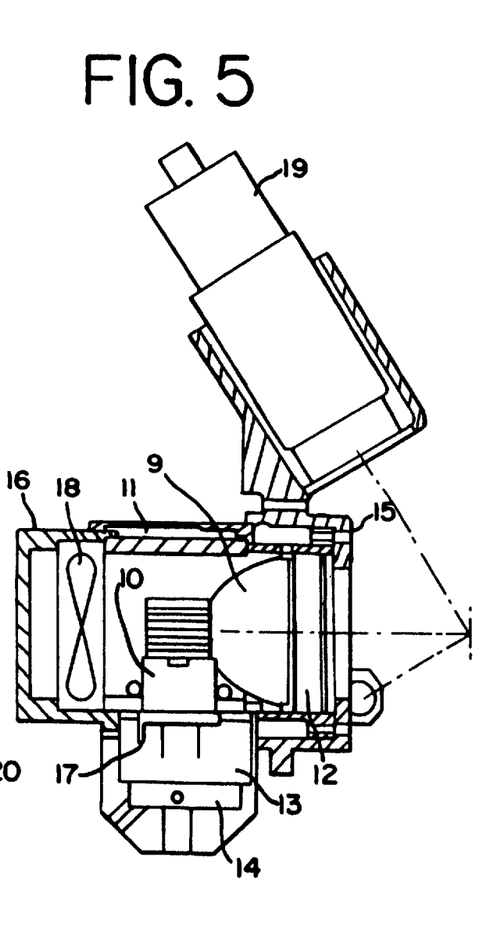
FIG. 5 is a top view of an assembled dolorimeter heating assembly in accordance with a preferred embodiment of the invention.

Reference is now made to FIGS. 4–5, the heatbeam dolorimeter comprises a heat projector 9, such as a Sylvania type DNE 150 watt, 24 volt, tungsten-halogen projector lamp, which gives approximately concentric radiance as measured by the naked eye when viewing the projected light on a screen 18 centimeters from the bulb. Other bulbs can be used having the same or similar projected radiance pattern and power-temperature profile, provided the bulb is first calibrated. The calibration criteria are that the bulb must create (i) a broad focal spot size of peak heat delivery of 20+/−0.2 mm at 5.08 centimeters from the edge of the lamp housing, measured using Sharp OF-20PrW thermal paper over 20 seconds exposure; and (ii) a temperature rise of 5.2+/−0.1 centigrade degrees at the calibrating thermocouple at the tenth second of irradiation.

The heat projector 9 is set in a lamp socket 10 inside a heat source housing assembly comprising a heat source cover 11, a stove 12, a carriage trap 13, a bottom cover 14, a front aperture cover 15, a back cover 16, and a carriage 17. The heat source housing assembly is preferably constructed of 2024 aluminum for optimal heat dissipation, except for the front aperture cover 15 of the housing, which is preferably milled from 1045 steel. Associated with the heat projector is a miniature cooling fan 18 within the posterior of the heat projector housing assembly. Also associated with the heat projector is an infrared sensing thermopile 19, such as an Omega OP65 device. The thermopile 19 receives electrical power from the battery 5 in the dolorimeter instrument package. Also associated with the heat projector are two laser positioning diodes 20 with integrated optics and driver, such as those made by Coherent Applied Laser Systems, part number 0220-058-00, with output power of 4.2 mW and an emission wavelength at 670 nM (visible, red). The laser positioning diodes 20 of the targeting device 19 receive electrical power from the battery 5 in the dolorimeter instrument package. The two positioning diodes 20 and the thermopile 19 are mounted 120 degrees from each other on the exterior of the heat projector housing.

Figure 6:
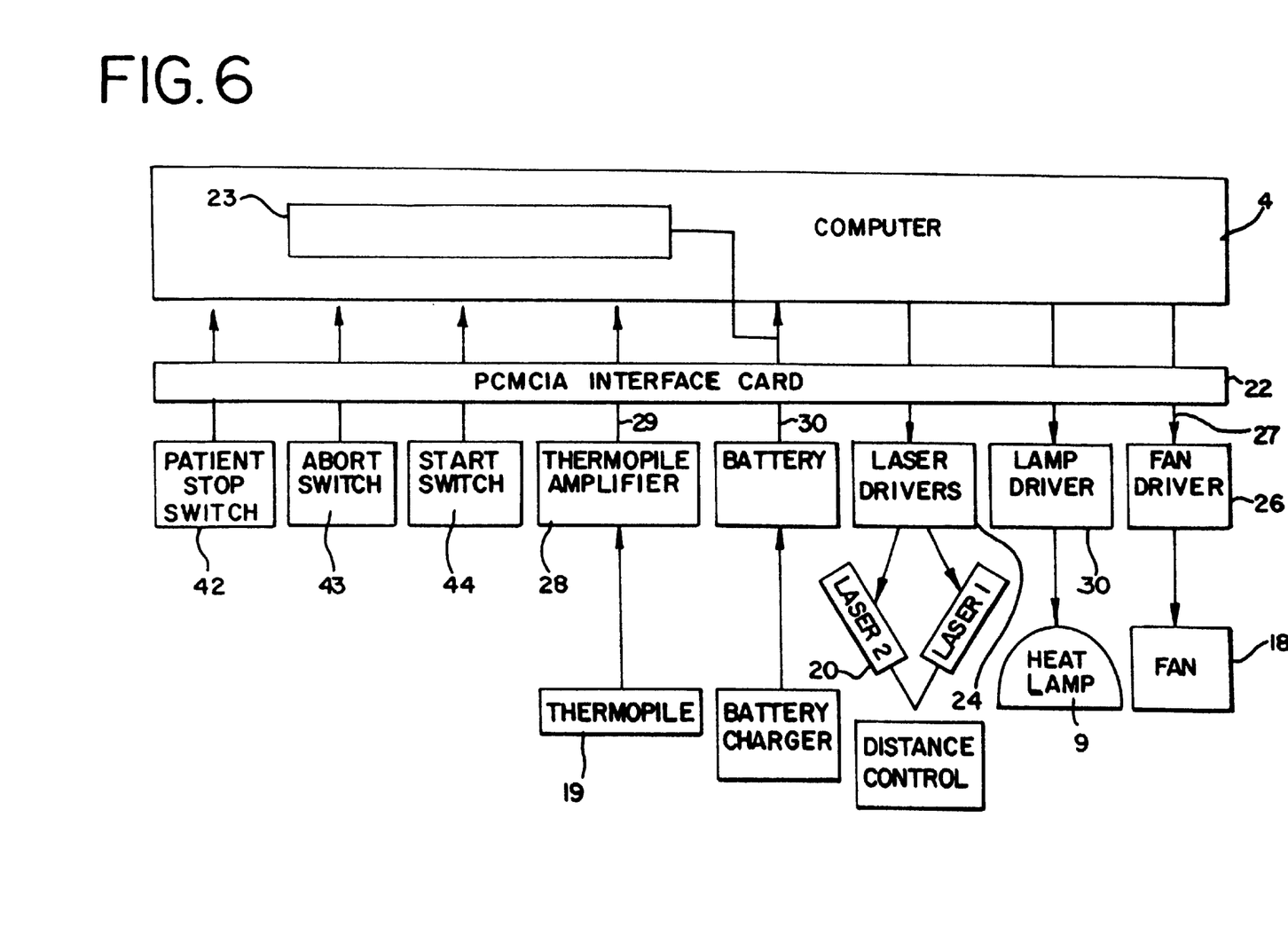
FIG. 6 is a block diagram of the computer connections with the dolorimeter apparatus in accordance with a preferred embodiment of the invention.

Referring now to FIG. 6, the heat projector 9 is controlled by a digital output connection, through the PCMCIA interface card 22 with the computer 4. The digital output controlling the heat projector has the capability of pulse frequency modulation. By having this digital output drive a one shot circuit, the pulse frequency is changed to pulse width modulation. This pulse width modulation is used to control the intensity of the heat beam. The computer determines the width of the pulse driving the heat projector using a calculation based on desired heat projector intensity and the battery voltage reading 23. As the battery is discharged, its voltage decreases and without some compensation, the heat projector intensity would also decrease. For this reason, the computer must modify the pulse width to compensate for the measured battery voltage.

The two laser positioning diodes 20 are connected to laser drivers 24 that are controlled by the computer 4 via a digital output connection 25 through the PCMCIA interface card 22. The miniature cooling fan 18 is connected to a fan driver 26 that is controlled by the computer 4 via a digital output connection 27 through the PCMCIA interface card 22. The infrared-sensing thermopile 19 is connected to an amplifier 28 delivering a signal which is related to the skin temperature target but not calibrated to read exact temperature. When the temperature measured by the thermopile 19 drops significantly, as occurs when the patient moves at their pain tolerance point, the heat projector 9 disengages and reports the time—the tolerance latency—to the database via a differential analog-to-digital input channel 29, through the PCMCIA interface card 22. The battery which powers the heat projector 9 also communicates to the computer via a differential analog-to-digital input channel 30 through the PCMCIA interface card 22.

The start button is depressed a second time and the lasers extinguish while the heat beam initiates 40. The heatbeam stimulus is stopped, and the "beam on" time recorded, either when the patient moves, as detected by the infrared sensing thermopile, or when the subject presses the patient stop button 42. A third button, the abort button, is pressed by the operator when some distracting event occurs in the room which could invalidate the reading. Referring to FIG. 6, the status of the stop 42, abort 43 and start buttons 44 are all communicated to the computer via a digital input connection through the PCMCIA interface card.

Figure 7:
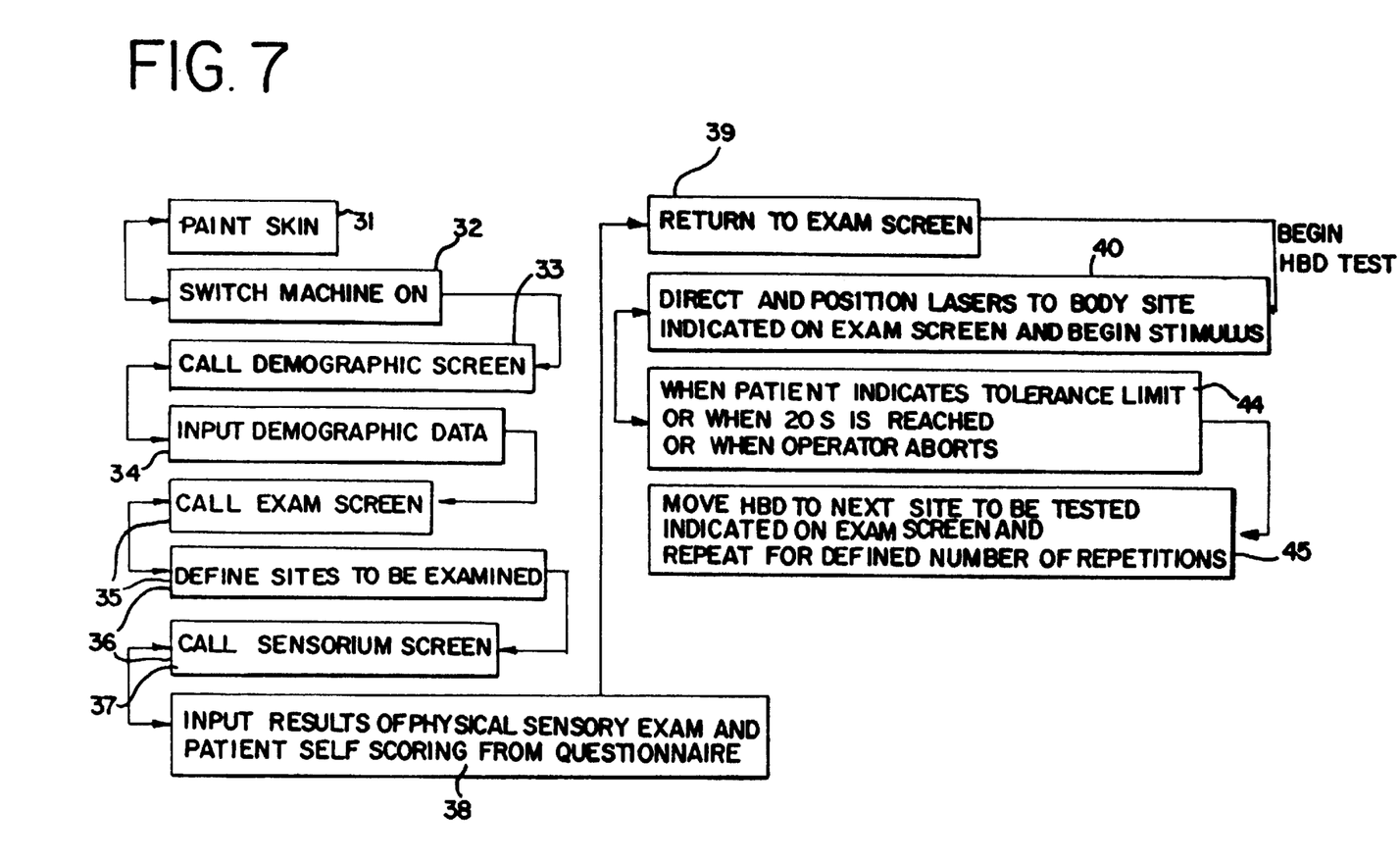
FIG. 7 is a flow chart detailing a method for determining a subject's cutaneous pain tolerance level at any site on the body in accordance with a preferred embodiment of the invention.

Referring now to FIG. 7, there is illustrated a method for determining a subject's cutaneous pain tolerance level at any site on the body in accordance with a preferred embodiment of the invention. The method comprises providing a portable, computerized heatbeam dolorimeter apparatus as disclosed above. An embodiment of the method comprises painting the subject's skin 31 at the site to be tested with a matt black skin stain, such as Avery-Dennison type 42 non-toxic ink, to enhance absorption of the radiant heat generated by the heat projector.

In a preferred embodiment, the computer software was written in Microsoft Visual Basic, running under Windows 95. Each screen (called a "Form") is provided with "buttons" to operate choices. The buttons are selected by the mouse on the computer. When the computer powers up 32 the first form displayed is called the MainHeat Form. This form provides selections to either calibrate the dolorimeter apparatus or to input demographic data for the experiment. The calibration form allows the operator to record the temperature caused by the heatbeam when focused on a temperature sensing device. The demographics screen 33 has text boxes for entry of relevant demographic data 34 concerning the subject. From the demographics form one can press a button to go to either the therapeutic exam setup form 35, for use when the subject is to be tested both before and after some type of therapy, or the standard exam setup form 35, which presents an outline of the subject's body with sites to be tested designated as such 36. This information is processed to the standard exam setup form, and the data is automatically entered into a table in the sensorium form 37, where the technician also inputs data from the subject's pain questionnaire 38. The recorded data is then archived to the database.

To measure tolerance latency at a particular site, the exam form 39 is recalled on the computer, and the heatbeam dolorimeter head is pointed at the approximate body site on the subject and the start button on the computer is depressed one time. The two laser diodes then illuminate and the dolorimeter head is adjusted so that the two laser beams converge at the center of the black spot on the subject's skin. The start button is depressed a second time and the lasers extinguish while the heat beam initiates 40. The heatbeam stimulus is stopped, and the "beam on" time recorded, either when the patient moves, as detected by the infrared sensing thermopile, or when the subject presses the patient stop button 41. A third button, the abort button, is pressed by the operator when some distracting event occurs in the room which could invalidate the reading. Referring to FIG. 6, the status of the stop 42, abort 43 and start buttons 44 are all communicated to the computer via a digital input connection through the PCMCIA interface card.

From the exam form, means are provided on the screen for going to the sensorium form where the data may be viewed to verify completeness before permanently saving it. From that screen, the operator may return to the demographics form and process another subject, or may test the next site indicated on the exam screen 45.

It will be appreciated by persons with skill in the art that the present invention is not limited to what has been particularly shown and described hereinabove. Rather, the scope of the present invention is defined only by the claims that follow:

What is claimed is:

1. An improved dolorimeter apparatus for determining pain tolerance at any site on skin of a subject's body, said apparatus comprising, in combination:

a non-contact heat source for projecting heat on a subject's skin;

means for controlling the rate of delivery of the heat to the skin;

remote means for detecting the temperature of the skin where it is heated by the heat source; and means for processing time and temperature readings detected by the remote means for detecting the temperature of the skin.

2. An improved dolorimeter apparatus for determining a subject's cutaneous pain tolerance level at any site on the body, said apparatus comprising:

a noncontact heat projector, set inside a housing assembly, for causing a controlled heating of the skin on said subject, to cause pain in said subject;

a targeting device, connected to said non-contact heat projector housing assembly, for determining the distance between said non-contact heat projector and a monitoring site on said subject;

a thermal sensing means, connected to said non-contact heat projector housing assembly, for detecting movement of said subject in response to said subject reaching said pain tolerance level;

a control means interconnected to said noncontact heat projector and said targeting device, for controlling the stimulus intensity of said non-contact heat projector and for controlling the output of said targeting device;

a data entry means for interfacing with said control means, allowing termination of stimulus intensity control by said control means;

a processing means responsive to said thermal sensing means movement detection, and to said data entry means for interfacing with said control means, to allow for automatic data acquisition regarding said pain tolerance level; and means for storing a data record of said pain tolerance level.

3. The improved dolorimeter apparatus of claim 2 further comprising an attachment arm for holding said non-contact heat projector housing assembly in place at the appropriate distance and angle to said subject's skin, said attachment arm connected to the base of said non-contact heat projector housing assembly, said attachment arm also connected to a moveable pivot base, said connections allowing for portability of said apparatus.

4. An improved dolorimeter apparatus for determining a subject's cutaneous pain tolerance level at any site on the body, said apparatus comprising:

a noncontact heat projector, set inside a housing assembly, for causing a controlled heating of the skin on said subject, to cause pain in said subject;

a targeting device, comprising two laser positioning diodes, connected to said non-contact heat projector housing assembly, for determining the distance between said non-contact heat projector and a monitoring site on said subject;

an infrared sensing thermopile, connected to said non-contact heat projector housing assembly, for detecting movement of said subject in response to said subject reaching said pain tolerance level;

a control means interconnected to said noncontact heat projector and said laser positioning diodes, for controlling the stimulus intensity of said non-contact heat projector and for controlling the output of said laser positioning diodes;

a data entry means for interfacing with said control means, allowing termination of stimulus intensity control by said control means;

a processing means responsive both to said infrared-sensing thermopile movement detection, and to said data entry means for interfacing with said control means, to allow for automatic data acquisition regarding said pain tolerance level; and means for storing a data record of said pain tolerance level.

5. The improved dolorimeter apparatus of claim 4 further comprising an attachment arm for holding said non-contact heat projector housing assembly in place at the appropriate distance and angle to said subject's skin, said attachment arm connected to the base of said non-contact heat projector housing assembly, said attachment arm also connected to a moveable pivot base, said connections allowing for portability of said apparatus.

6. The improved dolorimeter apparatus of claim 4, wherein said two laser positioning diodes and said infrared sensing thermopile are attached to the exterior of said non-contact heat projector housing assembly at intervals of 120 degrees from each other, such that said laser positioning diodes and said thermopile are focused on the same said monitoring site as said non-contact heat projector.

7. A method for detecting pain tolerance comprising:
(a) heating an area of a subject's skin using a heat source over a period of time in a controlled manner without contacting the skin with the heat source, to cause a pain sensation;
(b) measuring the temperature of the area where the heat is projected on the subject's skin over the time period of heating; and
(c) analyzing the temperature and time data to determine the subject's pain tolerance.

8. A method for determining a subject's cutaneous pain tolerance level at any site on the body, which comprises:
A) providing an apparatus consisting of:
a noncontact heat projector, set inside a housing assembly, for causing a controlled heating of the skin on said subject, to cause pain in said subject;
a targeting device, connected to said non-contact heat projector housing assembly, for determining the distance between said non-contact heat projector and a monitoring site on said subject;
a thermal sensing means, connected to said non-contact heat projector housing assembly, for detecting movement of said subject in response to said subject reaching said pain tolerance level;
a control means interconnected to said noncontact heat projector and said targeting device, for controlling the stimulus intensity of said non-contact heat projector and for controlling the output of said targeting device;
a data entry means for interfacing with said control means, allowing termination of stimulus intensity control by said control means;
a processing means responsive both to said thermal sensing means movement detection, and to said data entry means for interfacing with said control means, to allow for automatic data acquisition regarding said pain tolerance level; and
means including a memory for storing a data record of said pain tolerance level;
B) using said targeting device, under control of said control means, to accurately position said non-contact heat projector on said subject at said monitoring site;
C) initiating a stimulus of a controlled intensity from said non-contact heat projector, under control of said control means;
D) and monitoring the time interval between initiation of said stimulus and detection by said thermal sensing means that the subject has reached said pain tolerance level, said interval, or the power-time integral thereof, being a measure of pain tolerance latency at said monitoring site, said pain tolerance latency data being automatically acquired by said processing means from said thermal sensing means.

9. The method of claim 8 further comprising providing an apparatus further comprising an attachment arm for holding said non-contact heat projector housing assembly in place at the appropriate distance and angle to said subject's skin, said attachment arm connected to the base of said non-contact heat projector housing assembly, said attachment arm also connected to a moveable pivot base, said connections allowing for portability of said apparatus.

10. The method of claim 8 further comprising processing of said pain tolerance latency data by said processing means to obtain statistical data, said statistical data stored by said memory means.

11. The method of claim 10 further comprising displaying said pain tolerance latency data and said statistical data on a display.

12. The method of claim 8 further comprising painting the skin of said subject with black ink at said monitoring site, to minimize reflection of the heatbeam stimulus.

13. A method for determining a subject's cutaneous pain tolerance level at any site on the body, which comprises:
A) providing a portable apparatus consisting of:
a noncontact heat projector, set inside a housing assembly, for causing a controlled heating of the skin on said subject, to cause pain in said subject;
a targeting device, comprising two laser positioning diodes, connected to said non-contact heat projector housing assembly, for determining the distance between said non-contact heat projector and a monitoring site on said subject;
an infrared sensing thermopile, connected to said non-contact heat projector housing assembly, for detecting movement of said subject in response to said subject reaching said pain tolerance level;
a control means interconnected to said noncontact heat projector and said laser positioning diodes, for controlling the stimulus intensity of said non-contact heat projector and for controlling the output of said laser positioning diodes;
a data entry means for interfacing with said control means, allowing termination of stimulus intensity control by said control means;
a processing means responsive to said infrared-sensing thermopile movement detection, and to said data entry means for interfacing with said control means, to allow for automatic data acquisition regarding said pain tolerance level; and
means for storing a data record of said pain tolerance level.
B) using said laser positioning diodes, under control of said control means, to accurately position said non-contact heat projector on said subject at said monitoring site;
C) initiating a stimulus of a controlled intensity from said non-contact heat projector, under control of said control means;

D) and monitoring the time interval between initiation of said stimulus and detection by said infrared-sensing thermopile that the subject has reached said pain tolerance level, said interval, or the power-time integral thereof, being a measure of pain tolerance latency at said monitoring site, said pain tolerance latency data being automatically acquired by said processing means from said thermopile.

14. The method of claim 13 further comprising providing an apparatus further comprising an attachment arm for holding said non-contact heat projector housing assembly in place at the appropriate distance and angle to said subject's skin, said attachment arm connected to the base of said non-contact heat projector housing assembly, said attachment arm also connected to a moveable pivot base, said connections allowing for portability of said apparatus.

15. The method of claim 13 further comprising processing of said pain tolerance latency data by said processing means to obtain statistical data, said statistical data stored by said memory means.

16. The method of claim 15 further comprising displaying said pain tolerance latency data and said statistical data on a display.

17. The method of claim 13 further comprising painting the skin of said subject with black ink at said monitoring site, to minimize reflection of the heatbeam stimulus.

* * * * *